(12) United States Patent
Vess

(10) Patent No.: US 8,257,289 B2
(45) Date of Patent: Sep. 4, 2012

(54) FITTING OF COMPRESSION GARMENT

(75) Inventor: Mark A. Vess, Hanson, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 393 days.

(21) Appl. No.: 12/699,610

(22) Filed: Feb. 3, 2010

(65) Prior Publication Data

US 2011/0190675 A1 Aug. 4, 2011

(51) Int. Cl.
*A61H 7/00* (2006.01)
(52) U.S. Cl. ......................... 601/152; 601/143
(58) Field of Classification Search ................ 601/1, 27, 601/136, 143, 148–152, 166; 602/13; 73/865.8; 324/245
See application file for complete search history.

(56) References Cited

U.S. PATENT DOCUMENTS

| | | |
|---|---|---|
| 3,866,604 A | 2/1975 | Curless et al. |
| 4,016,868 A | 4/1977 | Allison |
| 4,353,359 A | 10/1982 | Milbauer |
| 4,396,010 A | 8/1983 | Arkans |
| 4,469,099 A | 9/1984 | McEwen |
| 4,492,234 A | 1/1985 | Arkans |
| 4,605,010 A | 8/1986 | McEwen |
| 4,671,290 A | 6/1987 | Miller et al. |
| 5,010,893 A | 4/1991 | Sholder |
| 5,050,613 A | 9/1991 | Newman et al. |
| 5,052,375 A | 10/1991 | Stark et al. |
| 5,103,833 A | 4/1992 | Apple |
| 5,167,237 A | 12/1992 | Rabin et al. |
| 5,233,987 A | 8/1993 | Fabian et al. |
| 5,284,133 A | 2/1994 | Burns et al. |
| 5,331,548 A | 7/1994 | Rollema et al. |
| 5,443,440 A | 8/1995 | Tumey et al. |
| 5,459,700 A | 10/1995 | Jacobs |
| 5,474,083 A | 12/1995 | Church et al. |
| 5,514,079 A | 5/1996 | Dillon |
| 5,575,762 A | 11/1996 | Peeler et al. |
| 5,591,200 A | 1/1997 | Cone et al. |
| 5,718,232 A | 2/1998 | Raines et al. |
| 5,806,512 A | 9/1998 | Abramov et al. |
| 5,810,735 A | 9/1998 | Halperin et al. |
| 5,840,049 A | 11/1998 | Tumey et al. |
| 5,929,782 A | 7/1999 | Stark et al. |
| 5,968,073 A * | 10/1999 | Jacobs .......................... 606/202 |
| 5,982,285 A | 11/1999 | Bueche et al. |
| 6,047,203 A | 4/2000 | Sackner et al. |

(Continued)

FOREIGN PATENT DOCUMENTS

EP 0898475 B1 8/2002

(Continued)

OTHER PUBLICATIONS

European Search Report regarding related application serial No. EP 11152713.1 dated Jun. 1, 2011, 4 pgs.

(Continued)

*Primary Examiner* — Quynh-Nhu H Vu
(74) *Attorney, Agent, or Firm* — Thomas M. Johnston, Esq.

(57) ABSTRACT

Optimizing fit of a compression garment for use with a patient receiving compression therapy. Sensors formed on the garment detect characteristics of the fit of the garment in the vicinity of each sensor. The fit sensors may be capacitive disks imprinted on the garment. A controller computes overall fit of the garment on the patient based on signals from the sensors.

24 Claims, 9 Drawing Sheets

U.S. PATENT DOCUMENTS

| | | | |
|---|---|---|---|
| 6,051,016 A | 4/2000 | Mesaros et al. | |
| 6,102,874 A | 8/2000 | Stone et al. | |
| 6,135,106 A | 10/2000 | Dirks et al. | |
| 6,171,270 B1 | 1/2001 | Gau | |
| 6,188,407 B1 | 2/2001 | Smith et al. | |
| 6,200,265 B1 | 3/2001 | Walsh et al. | |
| 6,231,532 B1 | 5/2001 | Watson et al. | |
| 6,338,719 B1 | 1/2002 | Drzewiecki et al. | |
| 6,381,482 B1 | 4/2002 | Jayaraman et al. | |
| 6,387,065 B1 | 5/2002 | Tumey | |
| 6,416,471 B1 | 7/2002 | Kumar et al. | |
| 6,436,058 B1 | 8/2002 | Krahner et al. | |
| 6,440,093 B1 | 8/2002 | McEwen et al. | |
| 6,450,981 B1 | 9/2002 | Shabty et al. | |
| 6,468,237 B1 * | 10/2002 | Lina | 601/150 |
| 6,514,200 B1 | 2/2003 | Khouri | |
| 6,527,711 B1 | 3/2003 | Stivoric et al. | |
| 6,551,252 B2 | 4/2003 | Sackner et al. | |
| 6,616,579 B1 | 9/2003 | Reinbold et al. | |
| 6,736,787 B1 | 5/2004 | McEwen et al. | |
| 6,775,577 B2 | 8/2004 | Crukovich et al. | |
| 6,805,667 B2 | 10/2004 | Christopherson et al. | |
| 6,858,012 B2 | 2/2005 | Burns et al. | |
| 6,953,440 B2 * | 10/2005 | Porrata et al. | 601/149 |
| 7,115,104 B2 | 10/2006 | Van Brunt et al. | |
| 7,118,534 B2 | 10/2006 | Ward et al. | |
| 7,214,192 B2 | 5/2007 | Poliac et al. | |
| 7,244,225 B2 | 7/2007 | Loeb et al. | |
| 7,354,411 B2 * | 4/2008 | Perry et al. | 602/13 |
| 7,398,803 B2 | 7/2008 | Newton | |
| 7,410,475 B2 * | 8/2008 | Krensky et al. | 604/29 |
| 7,425,203 B2 | 9/2008 | Van Brunt et al. | |
| 7,426,157 B2 | 9/2008 | Arnold et al. | |
| 7,637,879 B2 | 12/2009 | Barak et al. | |
| 7,771,376 B2 | 8/2010 | Roth et al. | |
| 2002/0087054 A1 | 7/2002 | Lin et al. | |
| 2003/0125649 A1 | 7/2003 | McIntosh et al. | |
| 2003/0135127 A1 | 7/2003 | Sackner et al. | |
| 2004/0030270 A1 | 2/2004 | Johnson | |
| 2004/0054306 A1 | 3/2004 | Roth et al. | |
| 2004/0127937 A1 | 7/2004 | Newton | |
| 2004/0199232 A1 | 10/2004 | Wallace et al. | |
| 2005/0033351 A1 | 2/2005 | Newton | |
| 2005/0107725 A1 | 5/2005 | Wild et al. | |
| 2006/0058716 A1 | 3/2006 | Hui et al. | |
| 2006/0122544 A1 | 6/2006 | Ciluffo | |
| 2007/0010749 A1 | 1/2007 | Meng | |
| 2007/0049853 A1 | 3/2007 | Adams et al. | |
| 2007/0083152 A1 | 4/2007 | Williams et al. | |
| 2007/0249977 A1 | 10/2007 | Bonnefin et al. | |
| 2008/0177159 A1 | 7/2008 | Gavriely | |
| 2008/0183095 A1 | 7/2008 | Austin et al. | |
| 2008/0188781 A1 | 8/2008 | Carkner et al. | |
| 2008/0281630 A1 | 11/2008 | Sekura | |
| 2008/0312522 A1 | 12/2008 | Rowlandson et al. | |
| 2009/0005703 A1 | 1/2009 | Fasciano | |
| 2009/0024062 A1 | 1/2009 | Einarsson | |
| 2009/0036786 A1 | 2/2009 | Gough et al. | |
| 2009/0048525 A1 | 2/2009 | Rogers et al. | |
| 2009/0063194 A1 | 3/2009 | Rosneck et al. | |
| 2009/0234265 A1 * | 9/2009 | Reid et al. | 602/61 |

FOREIGN PATENT DOCUMENTS

| | | |
|---|---|---|
| EP | 1645254 A1 | 4/2006 |
| EP | 2359785 A1 | 8/2011 |
| JP | 08280635 A | 10/1996 |
| WO | 00/00155 A1 | 1/2000 |
| WO | 03/007855 A1 | 1/2003 |
| WO | 2006043080 A1 | 4/2006 |
| WO | 2007041806 A1 | 4/2007 |
| WO | 2011112442 A1 | 9/2011 |

OTHER PUBLICATIONS

Gungor et al., "A New Micro-Controller based Wear-Time Monitor for Use with Removable Orthodontic Appliances", Proceedings of the 19th Annual International Conference—IEEE/EMBS, Oct. 30 thru Nov. 2, 1997. Chicago, IL, USA. 3 pages.

SCD Response Compression System Controller. http://www.kendallvasculartherapy.com/VascularTherapy/... Feb. 9, 2009, 1 page.

"Doctor Life Health Care". www.dsmaref.com. Undated. 41 pgs.

AIRCAST Inc., VenaFlow Operator's Manual, Apr. 4, 2001. 26 pgs.

"Compression Devices" www.mweb.com. vol. 67, No. 2, Feb. 2004. 2 pgs.

Orthofix Vascular Novamedix, "Take a step into the world of foot impulse technology" www.orthofix.com/avimpulse. Undated. 4 pgs.

Tyco/Healthcare Kendall, "SCD Express Compression System". Undated. 24 pgs.

Bogatin, "PCB Directions," Printed Circuit Design & Manufacture, Oct. 2003, vol. 20, Issue 10, Atlanta, GA, 1 page.

Kadiallah et al, "Impedance Control is Tuned to Multiple Directions of Movement," Conference Proceedings: Annual International Conference of the IEEE Engineering in Medicine & Biology Society, 2008:5358-61, Aug. 2008, 4 pages.

Prance, "Novel Sensor Enables Remote Biometric-Data Acquisition," Department of Engineering and Design—University of Sussex, 2008 SPIE, 2 pages.

* cited by examiner

FITTING OF COMPRESSION GARMENT

BACKGROUND

A major concern for immobile patients and like persons are medical conditions that form clots in the blood, such as, deep vein thrombosis (DVT) and peripheral edema. Such patients and persons often include those undergoing surgery, anesthesia, extended periods of bed rest, etc. These blood clotting conditions generally occur in the deep veins of the lower extremities and/or pelvis. These veins, such as the iliac, femoral, popiteal and tibial, return deoxygenated blood to the heart. When blood circulation in these veins is retarded due to illness, injury, or inactivity, for example, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary embolus can form from the fragment potentially blocking a main pulmonary artery, which may be life threatening.

Vascular compression systems find frequent use for improving blood flow in a targeted area of a patient's body (e.g., a limb, such as a leg, foot, or arm). A conventional compression system typically incorporates a compression garment for applying compressive forces to the targeted area. The system delivers intermittent or cyclic pulses of compressed air to at least one inflatable chamber in the garment, which in turn inflates and compresses the body part on which the garment is worn. The cyclic inflation of the compression garment provides a non-invasive method of prophylaxis to reduce the likelihood of incidence of DVT and to improve blood flow.

A major source of inefficiency in any compression system is the waste of energy required to inflate loosely fitted compression garments. Relatively large air volumes are required for establishing the fit during the initial fill and during each subsequent inflation to account for any gaps between the garment and the patient. A user, such as a nurse or the patient, adjusts straps, buckles, wraps, or the like on the garment in an attempt to achieve a comfortable yet effective fit. A crude approach used for determining good fit of the garment involves inserting one or more fingers into the space between the garment and the limb. In addition to a lack of precision, drawbacks of this approach include an inability to monitor fit during use and difficulty in adjusting fit to unusual limb profiles such as large muscles or swollen tissue.

SUMMARY

Briefly, a system for applying compression treatment embodying aspects of the invention comprises a garment sized and shaped to be wrapped around substantially a body part of a wearer. The garment has one or more fasteners for securing the garment in a self-retaining wrapped configuration around the body part and one or more selectively inflatable bladders for applying compression to the body part upon inflation. The system also includes at least one capacitive sensor formed on the garment. The sensor generates a signal indicative of a gap between the garment and the body part when the garment is in the wrapped configuration. A compression control unit, which includes a pump for pressurizing fluid, delivers pressurized fluid to the inflatable bladders via an outlet port in fluid communication with the pump. The compression control unit also includes one or more processors receiving and responsive to the signal from the capacitive sensor for evaluating an overall fit of the garment on the body part based on the gap between the garment and the body part.

In an aspect, a compression garment assembly includes a compression garment adapted for placement on a body part. The garment has at least one selectively inflatable bladder for applying compression to the body part upon inflation. The assembly also includes a plurality of capacitive sensors formed on the garment. Each capacitive sensor generates a signal indicative of a gap between the garment and the body part when the garment is placed thereon. The sensors define one or more areas of local fit specified for proper operation, each area having at least one of the plurality of capacitive sensors formed thereon. The generated signal from each of the capacitive sensors is indicative of a gap between the garment and the body part in the respective area of local fit. The assembly also includes a compression control unit for selectively inflating the bladder. A processor of the control unit is operatively connected to the plurality of capacitive sensors and configured for indicating proper fit of each of the one or more areas of local fit on the body part as a function of the generated signals from the capacitive sensors. In this manner, the compression garment assembly improves efficacy of compression treatment.

A method of monitoring use of a compression garment by a patient embodies further aspects of the invention. The method includes receiving a signal generated by a capacitive sensor formed on the garment, where the signal is indicative of a gap between the garment and the patient during use. The method also includes evaluating the signal from the one or more sensors to determine an overall fit of the garment on the limb based on the gap between the garment and the patient. And the method includes determining use of the compression garment by the patient and generating compliance efficacy data as a function of the determined overall fit and the determined garment use.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
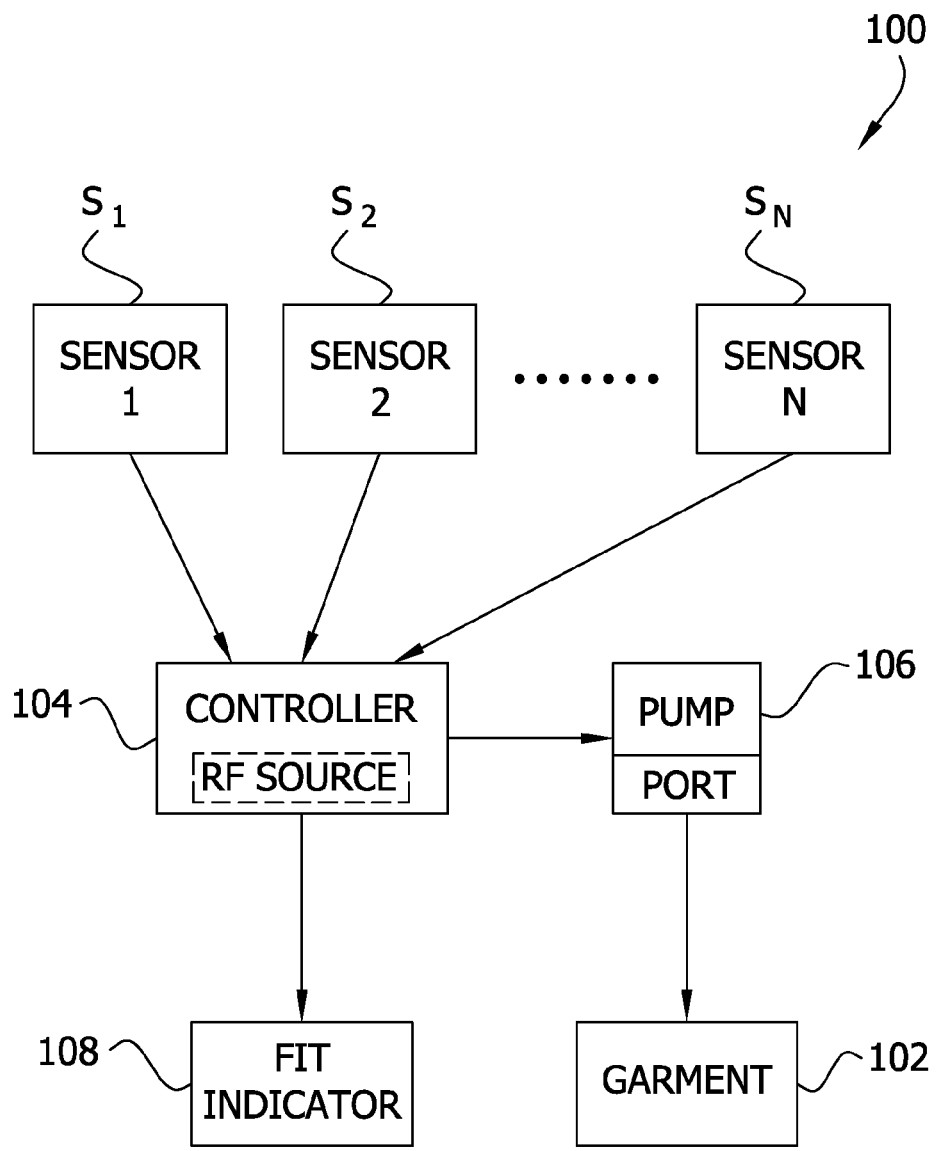
FIG. 1 is a schematic of a system for applying compression treatment to a patient.

FIG. 1 conceptually illustrates a system, generally designated 100, for applying compression treatment to a patient according to an embodiment of the invention. The system 100 comprises a compression garment 102, a controller 104, and a pump 106. The controller 104 controls operation of the pump 106 to selectively inflate the garment 102 via tubing connected to an outlet port (also designated by reference character 106). The controller 104 is also adapted to receive signals from multiple fit sensors $S_1$-$S_N$ and to indicate, via a fit indicator 108, a fit of garment 102 during use on a patient as a function of signals generated by the fit sensors $S_1$-$S_N$.

Figure 2:
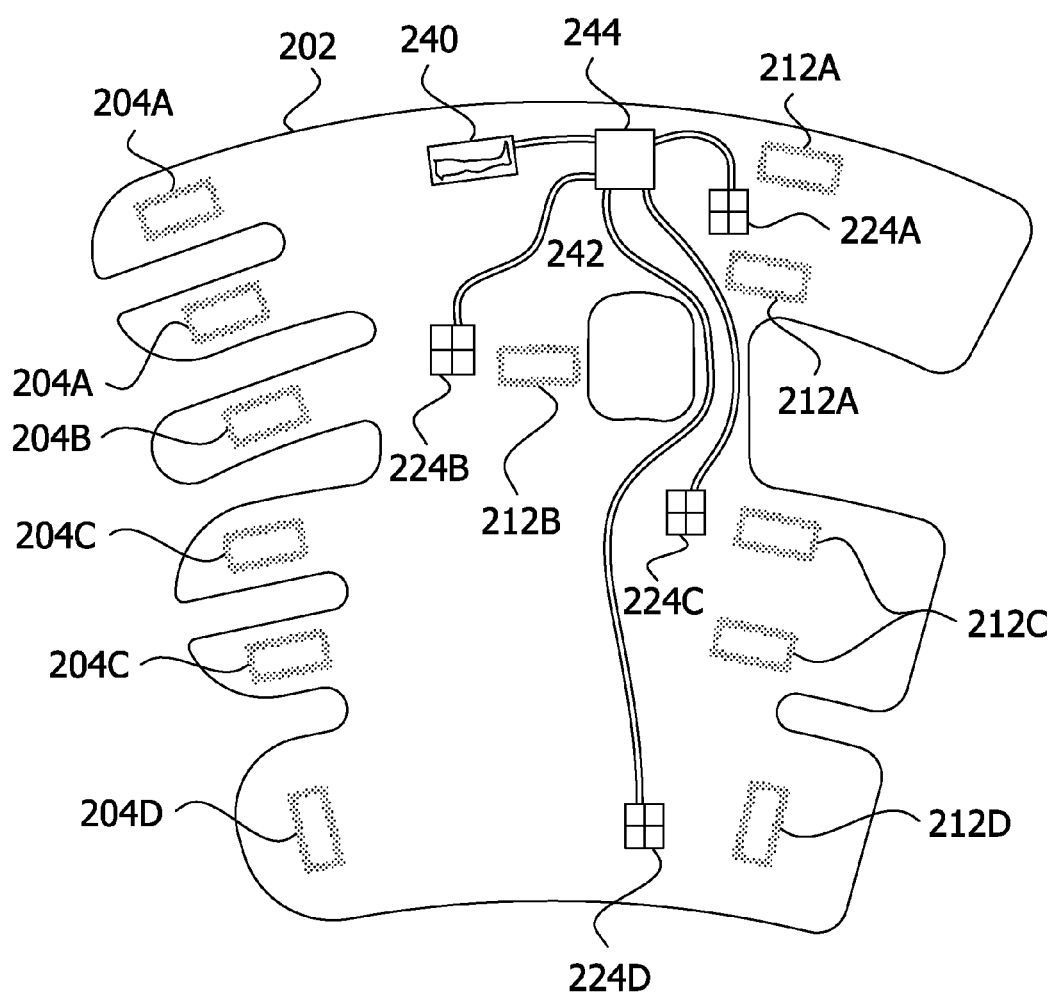
FIG. 2 is a front view of a compression garment in an unwrapped configuration according to an embodiment of the invention.
Figure 3:
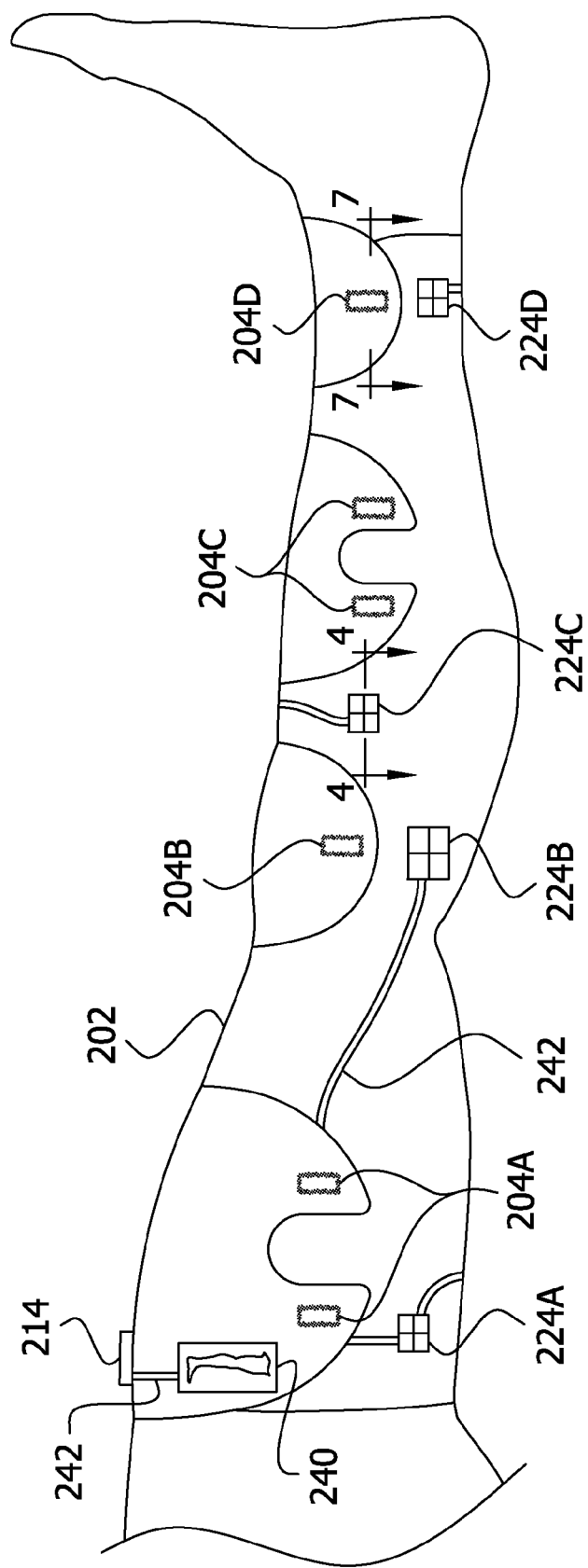
FIG. 3 illustrates the compression garment of FIG. 2 during use.

Referring to FIG. 2, a compression garment embodying aspects of the invention is designated generally 202 and is illustrated in an unwrapped configuration. FIG. 3, on the other hand, illustrates the garment 202 as worn on a patient's body part in a wrapped configuration during use for applying intermittent, selective compression. As shown in FIG. 3, garment 202 is worn on the patient's leg, for example.

Referring again to FIG. 2, compression garment 202 comprises one or more inflatable bladders (not shown) for selectively applying compression to the patient's body part (e.g., leg). Any number, shape, and configuration of the inflatable bladders is within the scope of the invention. The garment 202 also comprises one or more sets of fasteners 204A-D, 212A-D for securing the garment in place on the patient in a self-retaining configuration. FIG. 2 illustrates hook (204A-D) and corresponding loop (212A-D) tabs for this purpose. Alternatively, the fasteners may include other means such as buckles and/or hook and loop wraps. Any positioning device is within the scope of the invention.

Desirably, garment 202 has one or more specified areas of local fit. As described above, an ill fitted garment wastes precious air volume and pump energy for filling undesirable gaps. The garment 202 also includes a fit optimizing mechanism adapted for use when the garment is placed on the patient. In one embodiment, the fit optimizing mechanism comprises fit sensors 224A-D, a fit indicator panel 240, conductive traces 242, and a controller 244. As will be described in detail later, signals from the fit sensors 224A-D are monitored to establish, improve, and/or monitor fit of garment 202 on the leg of the patient. In the illustrated embodiment, each area of local fit has a fit sensor (e.g. 224A) and a corresponding fastener (204A, 212A) formed in its immediate vicinity for adjustment and monitoring during use. Such areas relate to typical voids formed when garment 202 is placed on the patient. As best illustrated in FIGS. 2 and 3, examples of such areas of fit for a leg may include the top of the calf when a leg sleeve is used (fastener 204C, 212C and sensor 224C), between the calf and the ankle (fastener 204D, 212D and sensor 224D), and both the top (fastener 204A, 212A and sensor 224A) and bottom (fastener 204B, 212B and sensor 224B) of the thigh when a thigh compression bladder is used. FIG. 3 generally illustrates sensors 224A-D formed at each of these locations as indicated by the abovementioned reference characters. In an embodiment, each inflatable bladder of garment 202 may have a sensor formed thereon. Variations of the garment design (e.g., number and shape of bladders, placement of fasteners, etc.) are within the scope of the invention.

The garment 202 further comprises the compression controller 244 attached or otherwise integrated thereon for operating the garment. The controller 244 is preferably sized for ease of use and without being cumbersome or a hindrance to patient mobility. The controller 244 also preferably comprises the pump/port 106 (see FIG. 1) for delivering pressurized air to garment 202, and associated tubing (not shown) for delivering the pressurized air to the garment. Alternatively, as illustrated in FIG. 1, the pump may be formed on the garment separate from the controller (e.g., pump 106 and controller 104). The tubing is desirably flush with the surface of the garment or hidden within the garment, and may be elastic in nature to accommodate stretching due to patient movement. The controller 244 further comprises one or more processors (not shown) for performing various functions associated with operating the garment 202, including (but not limited to) garment fit sensing and monitoring, patient compliance, etc. Preferably, a protective housing shields controller 244. Those skilled in the art are familiar with a variety of suitable processors for implementing the control and monitoring functions of controller 244. Desirably, the processor of controller 244 consumes minimal power and has a sleep mode. Also, the processor may be operable to accept analog inputs from sensors, such as capacitive frequency and/or current load, as well as digital inputs. The processor may also be capable of providing varied output, including display signals, audio signals, and historical information. Historical information may be utilized for measuring system parameters, such as efficacy.

Still referring to FIG. 2, one or more of the fit sensors 224A-D are formed on garment 202 for evaluating fit of the garment on the patient. In a preferred embodiment, fit sensors 224A-D are patches of printed-on conductive elements, though other forms of sensors are within the scope of the invention. The sensors 224A-D may be formed on or near the areas of local fit of garment 202. In this manner, sensors 224A-D may be used to evaluate and monitor fit in the most critical areas as specified by the garment manufacturer for efficient operation.

Each of the sensors 224A-D are connected to controller 244 via the connecting elements or traces 242, as illustrated. Preferably, the connection is made via printed wiring, similar to PCB (Printed Circuit Board) technology, on garment 202 itself. In this manner, the use of bulky and winding wires is eliminated, aiding the compaction of garment 202. Other means of connecting controller 244 to sensors 224A-D, including wireless means, are within the scope of the invention.

Figure 4:
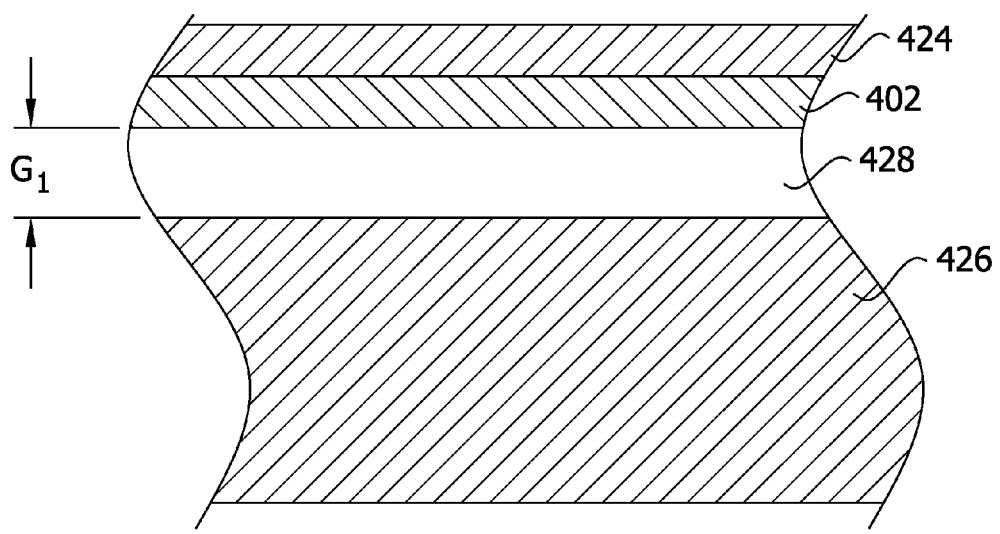
FIG. 4 is an enlarged section taken in the plane 4-4 of FIG. 3.

Referring now to FIG. 4, aspects of the invention are shown with respect to a garment 402. A radio frequency (RF) source of controller 244 may be used to generate an RF signal for application to sensors 224A-D, thereby completing a RF circuit. In this manner, as best illustrated in FIG. 4 for a single sensor 424, each sensor 424 formed on the garment 402 functions as a capacitive disk, also indicated by reference character 424. As the disk 424 is moved closer to a patient's body part, as indicated at 426, the RF energy from the disk 424 is absorbed into the patient as a function of a gap 428 of spacing $G_1$ as illustrated. This in turn creates a load in the RF circuit that varies according to the spacing $G_1$, i.e., capacitive coupling of disk 424 to the patient 426. The RF absorption current generated by disk 424 is collected and monitored by controller 244, and an appropriate algorithm converts the current values to a fit value. In an embodiment, a current shunt delivers the RF from controller 244 to capacitive sensors 224A-D. Since the patient acts as a sink for the RF energy, a large level of circulating RF energy may be required to maintain the signal level of the RF circuit. Current shunts are beneficial for measurement and delivery of these large current values, and are further considered more accurate and economical than equivalent Hall effect current sensors, for example.

In an alternative embodiment, as gap 428 varies, the frequency of the RF circuit formed by the RF source, disk 424, and patient 414, varies as a function of the gap 410. An appropriate algorithm then monitors the changing frequency to determine a fit value.

Referring again to FIGS. 2 and 3, a fit value of the local fit of garment 202 around each of sensors 224A-D, as well as a combined fit value corresponding to signals from all sensors 224A-D, may be calculated in any means possible. In a preferred embodiment, each of the sensors 224A-D is formed near a corresponding fastener 204A-D as illustrated, and corresponds to an area of desired local fit as discussed earlier. Fit is then evaluated by comparing the RF signal from sensor 224A (for example) to an acceptable value for the corresponding area of local fit, and if the signal exceeds the known value (i.e., thresholding), an acceptable local fit for sensor 224A is indicated.

Figure 5:
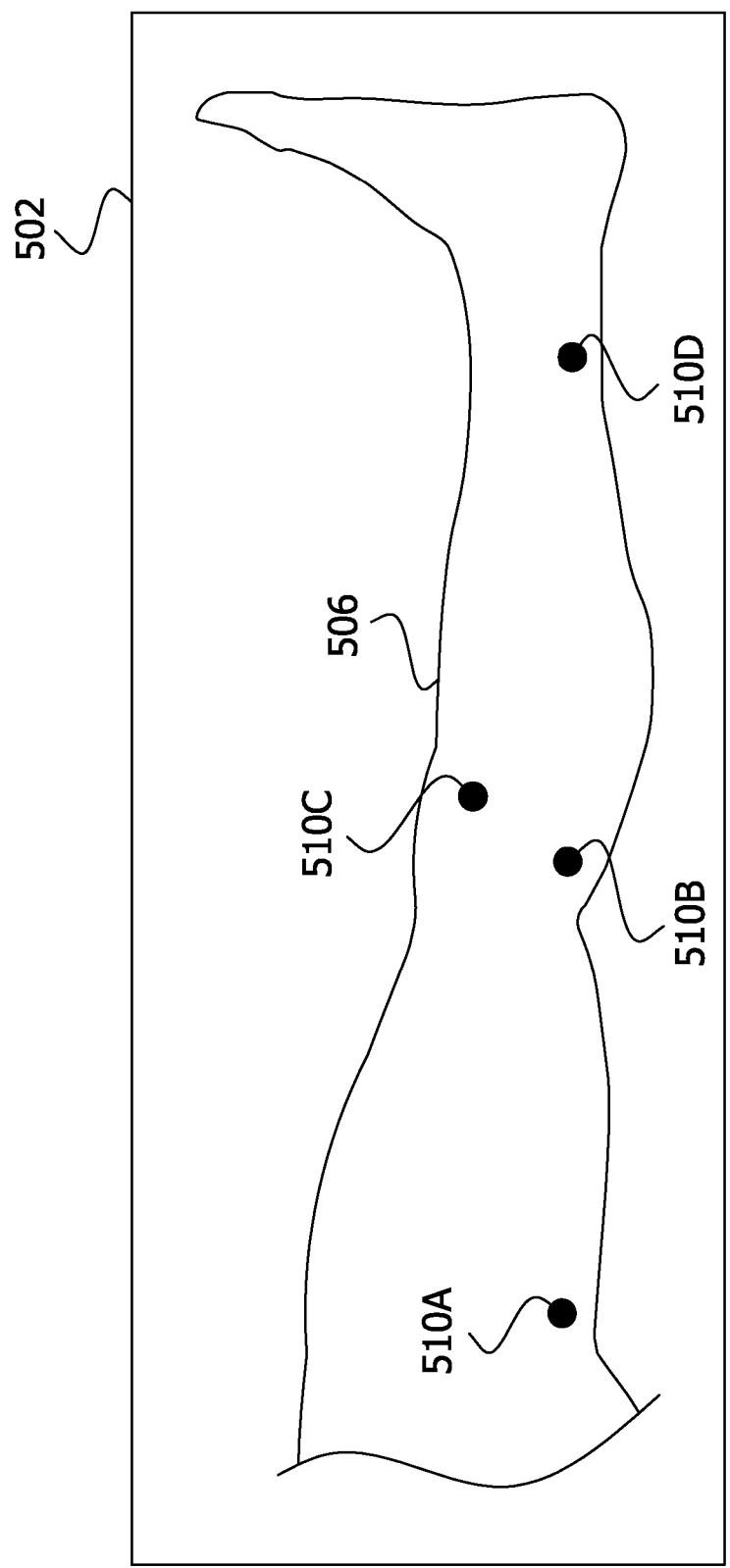
FIG. 5 is a front view of a fit indicator according to an embodiment of the invention.

Fit may be indicated to a user by several means. In an embodiment, a visual indicator is employed. Referring to FIGS. 2 and 3, and as best illustrated in FIG. 5, a light emitting diode (LED) panel 502 is formed on the garment 202 and operatively connected to controller 244. The panel 502 comprises multiple LEDs 510A-D, each corresponding to one of the capacitive sensors 224A-D. As the RF signal from sensor 224A (for example) reaches its acceptable value, the corresponding LED 510A lights up to indicate acceptable fit. The user adjusts fasteners 204A-D, 212A-D near the sensors 224A-D until all the LEDs 510A-D are lit, indicating that proper fit of the garment 202 has been achieved. The LEDs 510-A-D may be arranged in any manner on the display panel 502. A graphical overlay, for example, provides a visual indication mapping the location of each of the LEDs 510A-D to sensors 224A-D. FIG. 3 illustrates a preferred arrangement where LEDs 510A-D are arranged to visually aid the user. In an alternative embodiment, the LED panel may be formed on the controller itself. In yet another embodiment, the visual indicator is integral to the controller, such as an LCD display on the body of the controller that may also include other controller features.

In an alternative embodiment, an audible indicator is employed to signal overall fit of garment 202 as determined by sensors 224A-D. An audible tone heard by the user while fitting garment 202 indicates optimum fit. As the overall fit (determined by calculating an overall fit value from all of the sensors 224A-D) improves, the tone increases in pitch perceptibly. When all of the sensors 224A-D detect acceptable fit, the tone goes silent. Other alternative modifications to the audible tone (e.g., volume, tone) to indicate change in fit are possible and within the scope of the invention.

Figure 6A:
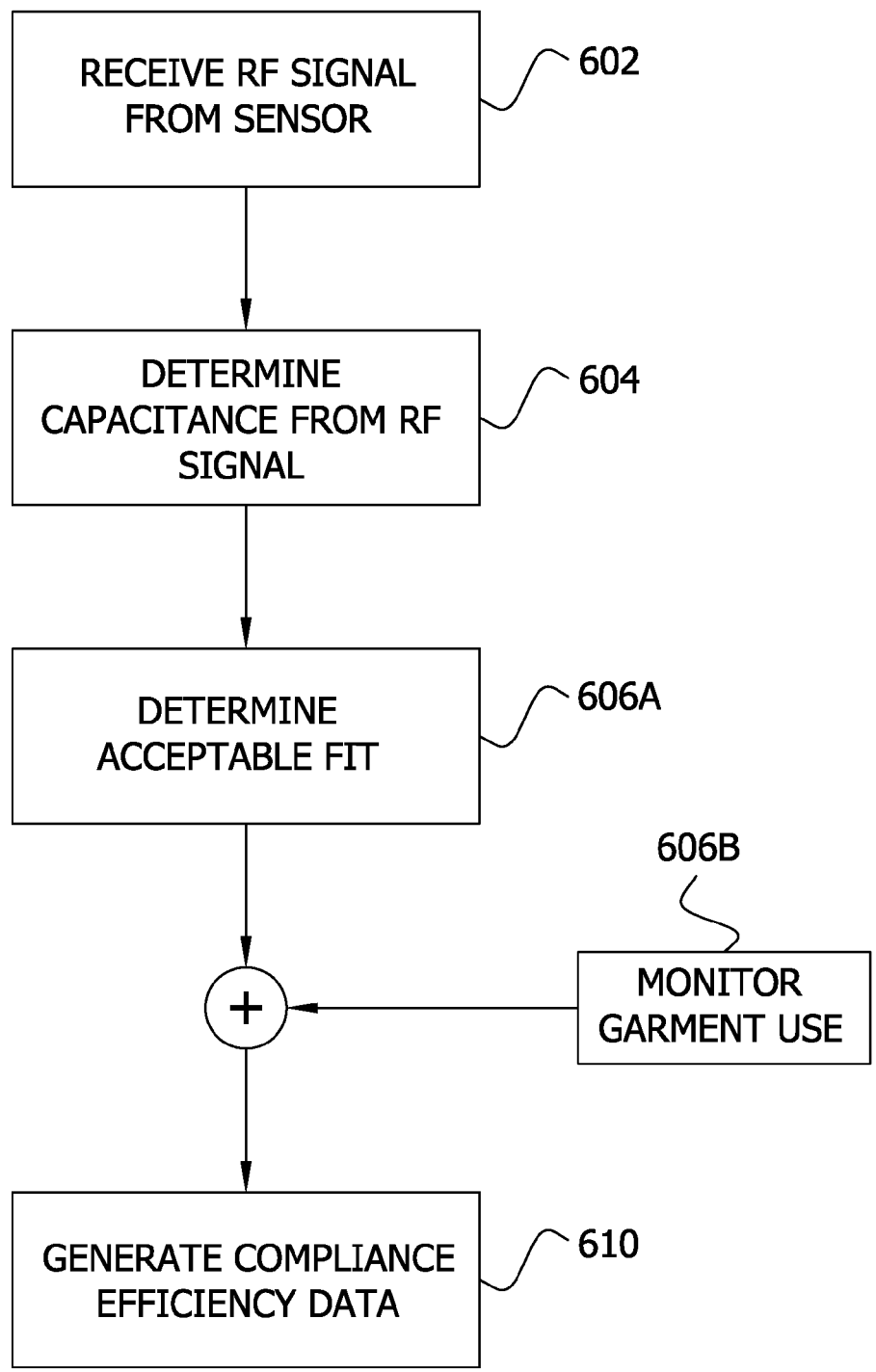
FIG. 6A is an exemplary flowchart for generating compliance efficiency data according to an embodiment of the invention.

A method of monitoring the use of compression garment 202 of FIGS. 2 and 3 by a patient according to one aspect of the invention is generally illustrated in FIG. 6A. At 602, controller 244 of garment 202 receives the RF signal from one of the sensors 224A-D, such as sensor 224A as described earlier. For the purpose of explanation one sensor 224A will be described, although the method is easily extensible to multiple sensors 224A-D. As described earlier with respect to FIG. 4, the received RF signal is indicative of the spacing $G_1$ of gap 428 between sensor 424 and patient body part 426. At 604, the RF signal is converted to capacitance, and at 606A, controller 244 compares the estimated capacitance versus an acceptable, threshold or recommended value. The controller 244 then determines whether or not garment 202 has an acceptable fit.

The controller 244 concurrently monitors the use of garment 2020 by the user along with the RF signal from sensor 224A at 606B. Monitoring of garment use may be performed by any means known in the art, including pressure sensors, temperature sensors, conductive hook and loop fasteners that complete an electrical circuit, and the like. In an example, pressure sensor data is used to determine the pressure applied as a measure of compliance. Then, at 610, controller 244 correlates the fit information from sensor 224A with the compliance information to determine the efficacy of therapy, and/or the quality of compliance.

Figure 6B:
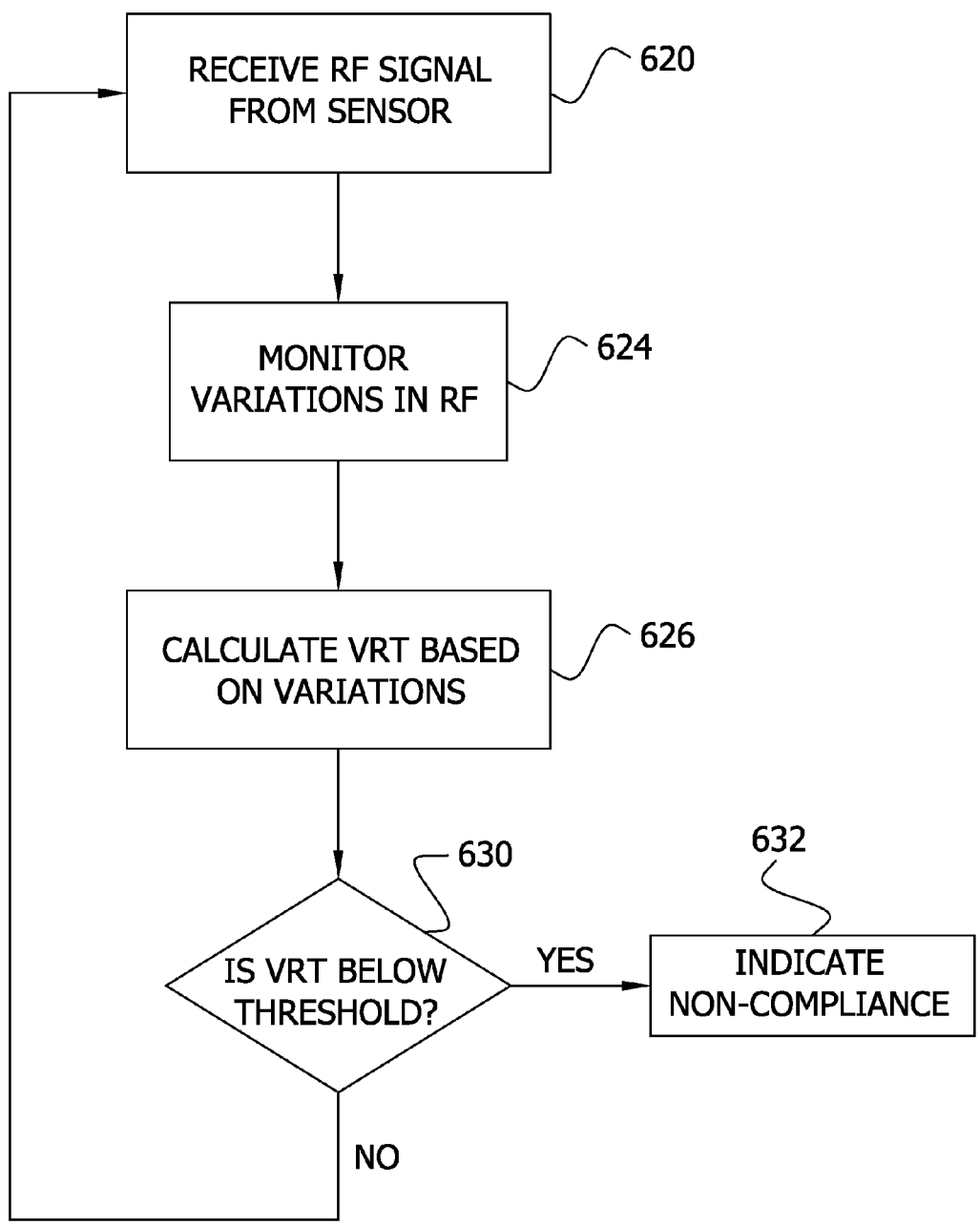
FIG. 6B is an exemplary flowchart for monitoring compliance according to an embodiment of the invention.

FIG. 6B illustrates an embodiment where the RF signal from one or more of the sensors 224A-D, such as sensor 224A, may be used for compliance monitoring. During a compression cycle, the limb exerts comparatively greater pressure against garment 202 as a function of venous refill thereby reducing the spacing $G_1$. That is, blood removed from a limb during a compression cycle returns to the limb thereafter. A measurable venous refill time (VRT) is associated with most compression therapies. This periodic change in the gap 410 caused by venous refill can be detected as periodic variations in the RF signal from sensor 224A. The controller 244 receives the RF signal at 620 from sensor 224A and, at 624, monitors variations in the received RF signal over time. The VRT value can be calculated from these variations at 626. The calculated VRT is compared against normal values, 30-60 seconds for example, at 630. If the VRT is above the upper limit, it is assumed that the patient is not wearing garment 202, and non-compliance is indicated at 632.

Figure 7:
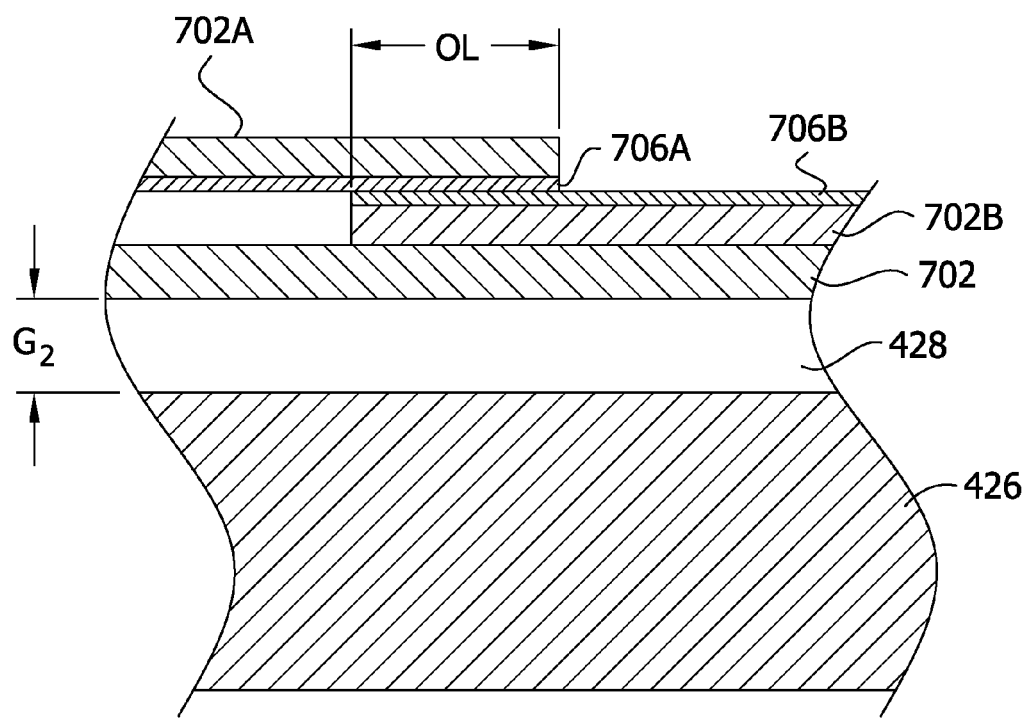
FIG. 7 is an enlarged section taken in the plane 7-7 of FIG. 3 according to an embodiment of the invention.

In an alternative or additional embodiment, controller 244 is further operable to challenge the size of a garment 702 for the patient. As illustrated in FIG. 7, this embodiment involves designing the fasteners of the garment 702 as overlapping upper and lower tabs 702A, 702B, respectively. Each of the tabs 702A-B has a conductive strip 706A, 706B, respectively, printed thereon. The tabs 702A-B may have hook and loop structures formed thereon, or other means of attachment to each other. The strips 706A-B align with each other during application of garment 702, forming in effect a variable capacitor. Increasing wrap of the garment 702 leads to increased area of overlap OL between the conducting strips 706A-B, and hence leads to greater measured capacitance. The controller 244 measures this capacitance and, if it exceeds a upper value (indicating significant overlap), controller 244 indicates to the user that garment 702 is too big for use. On the other hand, if the capacitance is too low (little overlap), controller 244 indicates to the user that garment 702 is too small, and that a larger size is recommended.

Figure 8:
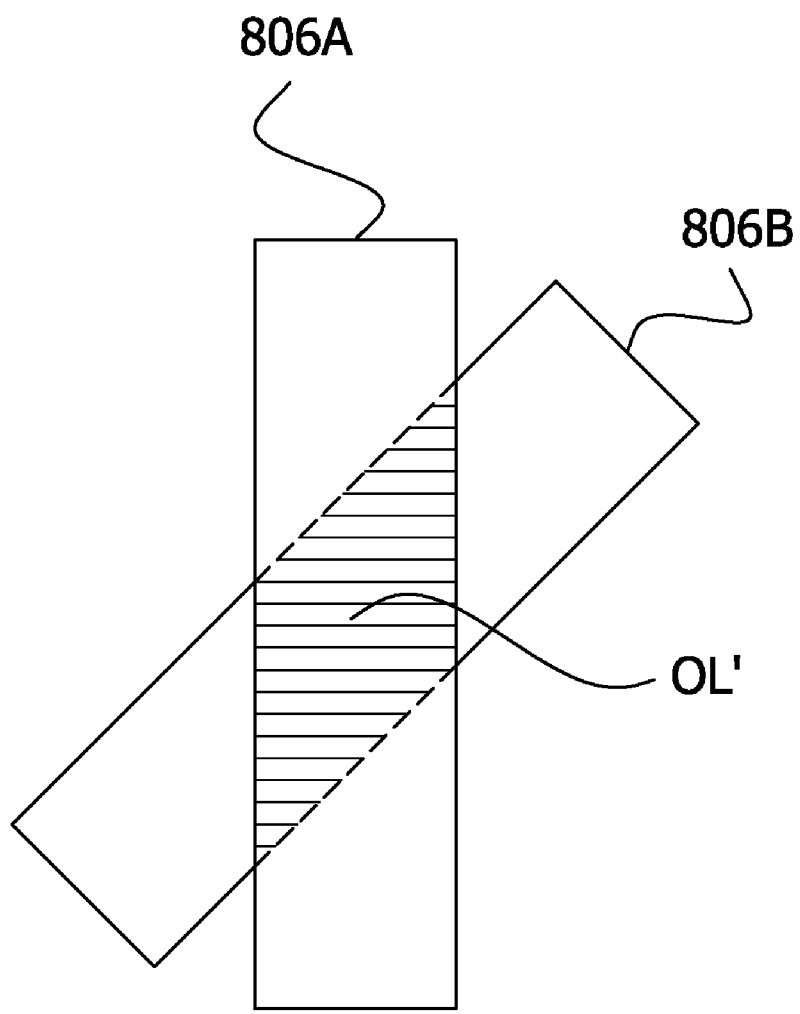
FIG. 8 is a top view of overlapping conductive strips to illustrate relative alignment and overlap of the conductive strips according to an embodiment of the invention.

Additionally or alternatively, if strips 706A-B are not aligned correctly, an error code is generated. In an embodiment such as illustrated in FIG. 8, the conductive strips 806A-B (corresponding to conductive strips 706 A-B) are sufficiently narrow to effect a steep decrease in area of overlap OL' (corresponding to area OL) and the measured capacitance, if the corresponding tabs 702A-B (not shown in FIG. 8 for clarity) are not aligned correctly. In an alternative embodiment (not shown), line markings on the tabs 702A-B are provided to aid the user in correct alignment of the fasteners. The measured capacitance is then a function of both the amount of overlap OL' and the correct alignment of strips 806A-B. As described above, an acceptable garment size and proper alignment are indicated to the user if this measured capacitance exceeds a threshold value.

Having described aspects of the invention in detail, it will be apparent that modifications and variations are possible without departing from the scope of the invention defined in the appended claims. For example, sensors 224A-D are ideally sized to be small enough for effective local fit indication but large enough to generate discernable signals. Conductive traces 242 can also have a capacitive value, which may skew the measured capacitance. The sensors 224A-D hence desirably have a large enough surface area to provide a significant component of the measured capacitance. In other words, a ratio between a surface area of the sensors 224A-D and a surface area of the traces 242 will determine the signal-tonoise (SNR) of the invention. In an embodiment, sensors 224A-D are approximately 15 mm diameter and disk-shaped. Alternatively, it is further possible for sensors 224A-D to be variably sized. In this manner, each sensor can be shaped and sized to conform to the specific area of fit measurement and monitoring.

As another example, the embodiments illustrated in FIGS. 6A and 6B may be combined, so that the RF signal from sensor 224A may be used for both fit estimation and compliance monitoring to generate the compliance efficacy data of FIG. 6A. This approach is beneficial for not requiring an additional sensor for determining compliance.

Referring again to FIGS. 2 and 3, sensors 224A-D and conductive traces 242 are preferably printed on elements as described. However, it is possible to design removable sensors that are attachable anywhere on garment 202. This design is beneficial for flexible deployment of sensors 224A-D.

Any suitable components may be used for constructing the printed on sensors and traces, given the requirements for flexibility, low profile and conductivity. In an embodiment, fit sensors 224A-D are volume conductive films constructed as a single layer of carbon-loaded polyethylene, thereby providing the benefits of humidity-independence and biocompatibility. Conductive traces 242 may be constructed from conductive fabrics that provide elasticity, such as the Novonic® and Tex|mate® from Amphenol Corporation. The display panel 502 may be constructed from low-profile films. For example, Nanofilm provides ultra-thin conductive nanocomposites comprising conductive nanoparticles in a clear, invisible film as thin as 1 micron. The film is conductive and flexible. Interconnections between the various components may be made through conductive and adhesive components, such as the 3M™ Anisotropic Conductive Film (ACF) adhesives that consist of thermoplastic and thermoset adhesives randomly loaded with conductive particles. Alternatively, or in addition, simpler solutions such as conductive, adhesive tapes (e.g. 3M™ Electrically Conductive Adhesive Transfer Tape, or ECATT) may be used.

To improve the patient experience, there is a trend towards miniaturization, and smaller and lighter vascular compression systems are being developed that integrate all components onto the compression garment itself. This presents a whole group of unique challenges. There is a cascading set of limitations that are immediately apparent to those familiar with the art. The controller must be reduced in size to be a comfortable fit on the garment and the patient's limb. As a result, smaller valves reduce the amount of air sent to the bladder, resulting in smaller bladder volumes. Most importantly, it is critical that these smaller devices still provide sufficient compression for effective therapy despite more limited compression abilities.

In view of the above, it will be seen that the several objects of the invention are achieved and other advantageous results attained. By initial and subsequent monitoring of the fit of the compression garments, it is assured that the compression garment, given its limited compression ability, is positioned to provide the most efficient transfer of compression forces possible to the patient. By placing multiple capacitive sensors in all areas of a garment deemed critical for establishing a proper fit, aspects of the invention can monitor areas that are not readily apparent to the user. By providing a visual and/or audio indicator, the user can readily receive feedback confirming or denying that a proper fit has been established. In this manner, the controller can be made operable if the garment is properly installed.

In operation, use of compression garment 202 by a patient is monitored by receiving signals generated by the capacitive sensors 224A-D. The signals are generally indicative of gaps between garment 202 and the patient during use. The received signals are evaluated to determine an overall fit of the garment 202 on the limb based on the gaps between the garment and the patient at each sensor location. The use of garment 202 by the patient is determined. Compliance efficacy data as a function of the determined overall fit and the determined garment use is then generated.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A system for applying compression treatment comprising:
  a garment for placement on a body part of a wearer, said garment comprising one or more selectively inflatable bladders for applying compression to the body part upon inflation;
  at least one capacitive sensor formed on the garment, said sensor generating a signal indicative of a gap between the garment and the body part when the garment is placed thereon; and
  a compression control unit for selectively inflating said one or more bladders, said control unit comprising:
    one or more processors receiving and responsive to the signal from the capacitive sensor for evaluating an overall fit of the garment on the body part based on the gap between the garment and the body part.

2. The compression system of claim 1, wherein the capacitive sensor is a printed-on conductive element formed on the garment.

3. The compression system of claim 1, wherein each inflatable bladder has at least one capacitive sensor formed thereon.

4. The compression system of claim 1, wherein the garment comprises one or more areas of local fit, and wherein each area of local fit has at least one corresponding capacitive sensor formed thereon.

5. The compression system of claim 4, wherein an adjustable fastener is formed near each capacitive sensor to adjust the local fit of the garment in the vicinity of the corresponding capacitive sensor.

6. The compression system of claim 5, where the adjustable fastener comprises at least one of the following: a hook and loop strap, a looped hook and loop strap, a hook and loop wrap, and a belt and buckle.

7. The compression system of claim 1, wherein the control unit further comprises a radio frequency (RF) signal generator for transmitting RF signals to each capacitive sensor.

8. The compression system of claim 7, wherein each capacitive sensor generates RF absorption current as a function of the gap between the capacitive sensor and the body part, said RF absorption current being indicative of local fit of the garment in the vicinity of the capacitive sensor.

9. The compression system of claim 7, wherein each capacitive sensor forms an oscillator circuit with the RF signal generator, wherein a resonant frequency of the oscillator circuit varies as a function of the gap between the capacitive sensor and the body part, said resonant frequency being indicative of local fit of the garment in the vicinity of the capacitive electrode.

10. The compression system of claim 1, wherein the control unit further comprises a fit indicator.

11. The compression system of claim 10, wherein the fit indicator comprises a plurality of visual indicators, each of said visual indicators corresponding to one of the capacitive sensors and being indicative of local fit of the garment in the vicinity of the corresponding capacitive sensor.

12. The compression system of claim 11, wherein the visual indicator is a light emitting diode.

13. The compression system of claim 10, wherein the fit indicator is an audible tone that increases in pitch as a function of overall fit of the garment.

14. The compression system of claim 1 comprising:
a plurality of said capacitive sensors formed on the garment, each of said capacitive sensors generating a signal indicative of a gap between the garment and the body part when the garment is placed thereon, said sensors defining one or more areas of local fit specified for proper operation, said areas each having at least one of the plurality of capacitive sensors formed thereon, wherein the generated signal from each of the capacitive sensors is indicative of a gap between the garment and the body part in the respective area of local fit;
said one or more processors configured for indicating proper fit of each of the one or more areas of local fit on the body part as a function of the generated signals from the plurality of capacitive sensors and thereby improving efficacy of compression treatment.

15. The compression system of claim 14, wherein the capacitive sensors are printed-on conductive elements formed on the compressive garment.

16. The compression system of claim 14, wherein an adjustable fastener is formed near each capacitive sensor to adjust the local fit of the corresponding area to achieve proper fit.

17. The compression system of claim 16, where the adjustable fastener comprises as least one of the following: a hook and loop strap, a looped hook and loop strap, a hook and loop wrap, and a belt and buckle.

18. The compression system of claim 14, further comprising a radio frequency (RF) signal generator for transmitting RF signals to each capacitive sensor.

19. The compression system of claim 18, wherein each capacitive sensor generates RF absorption current as a function of the gap between the capacitive sensor and the body part of the patient in the corresponding area of local fit.

20. The compression system of claim 18, wherein each capacitive sensor forms an oscillator circuit with the RF signal generator, wherein a resonant frequency of the oscillator circuit varies as a function of the gap between the capacitive sensor and the limb of the patient in the corresponding area of local fit.

21. The compression system of claim 14, wherein the controller further comprises a fit indicator.

22. The compression system of claim 21, wherein the fit indicator comprises a plurality of visual indicators, each of said visual indicators corresponding to one of the plurality of capacitive sensors and being indicative of proper fit of the garment in the corresponding area of local fit.

23. The compression system of claim 21, wherein the visual indicator is a light emitting diode.

24. The compression system of claim 21, wherein the fit indicator is an audible tone that increases in pitch as a function of overall fit of the compressive garment to the limb.

* * * * *